(12) United States Patent
Schröter

(10) Patent No.: US 12,357,157 B2
(45) Date of Patent: Jul. 15, 2025

(54) ENDOSCOPE WITH WORKING CHANNEL AND A CONTROL BODY

(71) Applicant: HOYA CORPORATION, Tokyo (JP)

(72) Inventor: Tilman Schröter, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 382 days.

(21) Appl. No.: 17/916,909

(22) PCT Filed: Mar. 29, 2021

(86) PCT No.: PCT/IB2021/052564
§ 371 (c)(1),
(2) Date: Oct. 4, 2022

(87) PCT Pub. No.: WO2021/205277
PCT Pub. Date: Oct. 14, 2021

(65) Prior Publication Data
US 2023/0148842 A1    May 18, 2023

(30) Foreign Application Priority Data

Apr. 9, 2020    (DE) ..................... 10 2020 109 966.5

(51) Int. Cl.
*A61B 1/00*    (2006.01)
*A61B 1/015*    (2006.01)

(52) U.S. Cl.
CPC ........ *A61B 1/0014* (2013.01); *A61B 1/00094* (2013.01); *A61B 1/015* (2013.01)

(58) Field of Classification Search
CPC ... A61B 1/0014; A61B 1/00094; A61B 1/015; A61B 1/00066; A61B 1/018; A61B 1/0052
See application file for complete search history.

(56) References Cited

U.S. PATENT DOCUMENTS

| 2005/0027165 | A1 | 2/2005 | Rovegno |
| 2006/0149129 | A1* | 7/2006 | Watts ................ A61M 25/0152 600/113 |
| 2006/0247494 | A1 | 11/2006 | Nakagawa et al. |

(Continued)

FOREIGN PATENT DOCUMENTS

| CN | 102740758 A | 10/2012 |
| CN | 107080513 A | 8/2017 |

(Continued)

OTHER PUBLICATIONS

International Search Report issued in International Bureau of WIPO Patent Application No. PCT/IB2021/052564, dated Jun. 9, 2021, along with an English translation thereof.

(Continued)

*Primary Examiner* — Anh Tuan T Nguyen
*Assistant Examiner* — Li-Ting Song
(74) *Attorney, Agent, or Firm* — GREENBLUM & BERNSTEIN, P.L.C.

(57) ABSTRACT

The invention relates to an endoscope with a working channel in an insertion tube, and a control body, on the distal side of which the insertion tube is connected, and an attachment body attached to the control body in a detachable manner, wherein the detachably fastenable attachment body includes a working channel assembly and a suction device assembly.

7 Claims, 7 Drawing Sheets

(56) References Cited

U.S. PATENT DOCUMENTS

| | | | |
|---|---|---|---|
| 2007/0276180 A1* | 11/2007 | Greenburg | A61B 90/57 600/106 |
| 2008/0021280 A1 | 1/2008 | Suzuki | |
| 2009/0082630 A1 | 3/2009 | Tulley | |
| 2012/0302835 A1 | 11/2012 | Mathieu et al. | |
| 2014/0296632 A1* | 10/2014 | Onuki | A61B 1/0125 600/107 |
| 2015/0057537 A1* | 2/2015 | Dillon | A61B 1/0014 600/113 |
| 2018/0168439 A1* | 6/2018 | Hibbs | A61B 1/126 |
| 2019/0104932 A1 | 4/2019 | Truckai et al. | |
| 2019/0239728 A1* | 8/2019 | Do | A61B 1/00133 |
| 2020/0077874 A1 | 3/2020 | Long et al. | |
| 2020/0214542 A1* | 7/2020 | Yoshinaga | A61B 1/00002 |
| 2020/0253460 A1* | 8/2020 | Yoshinaga | A61B 1/0125 |
| 2020/0253461 A1* | 8/2020 | Wang | A61B 1/00128 |
| 2020/0315426 A1* | 10/2020 | Yoshinaga | A61B 1/0055 |
| 2021/0386441 A1* | 12/2021 | Heimberger | A61B 1/00066 |

FOREIGN PATENT DOCUMENTS

| | | |
|---|---|---|
| CN | 209499689 U | 10/2019 |
| EP | 1882442 A1 | 1/2008 |
| JP | 2004-298358 A | 10/2004 |
| JP | 2005177208 A | 7/2005 |
| JP | 2005-237818 A | 9/2005 |
| JP | 2005-349186 A | 12/2005 |
| JP | 2008-541789 A | 11/2008 |

OTHER PUBLICATIONS

EPO Communication pursuant to Rules 161(1) and 162 EPC dated Nov. 16, 2022.
Office Action issued in Chinese Patent Application No. 202180027504.0, dated Oct. 28, 2024.
Office Action issued in Japanese Patent Application No. 2022-560517, dated Aug. 29, 2023, along with an English translation thereof.

* cited by examiner

ENDOSCOPE WITH WORKING CHANNEL AND A CONTROL BODY

The present invention relates to an endoscope with a working channel in an insertion tube, and a control body, on the distal side of which the insertion tube is connected.

In such an endoscope, the insertion tube is inserted into a patient for the purpose of an examination or a surgical intervention. Through the working channel, instruments can be guided through the insertion tube to a location at which the examination or surgical intervention is to take place.

After completing the examination or the surgical intervention, the insertion tube is pulled out. Thereafter, the endoscope is cleaned and sterilised so as to be ready for another use. Through cleaning and sterilisation, contamination as a result of previous use should be removed.

One objective is the invention is to create an endoscope with a working channel and a control body that is even more reliably cleaned of contaminants for another use.

This object is achieved by means of an endoscope with the features of claim 1. Advantageous further developments form the subject matter of the dependent claims.

The invention relates to an endoscope with a working channel in an insertion tube, a control body, on the distal side of which the insertion tube is connected, and an attachment body fastenable to the control body in a detachable manner, wherein the detachably fastenable attachment body comprises a working channel assembly and a suction device assembly.

In the case of such an endoscope, by detaching the detachably fastenable attachment body from the control body, the working channel assembly and the suction device assembly can be removed from the endoscope. The working channel assembly and the suction device assembly are particularly difficult to clean after use, so that in spite of cleaning and sterilisation, biofilms can form and persist on the surfaces. Thus, precisely those elements, on the surfaces of which there is an increased danger of the formation of biofilms due to use in the patient, are removed from the endoscope. The endoscope can therefore better prevent the transmission of germs arising from resistant biofilms.

The working channel assembly can comprise the working channel, which extends to the distal end of the endoscope. The suction device assembly can comprise a suction line and a suction control valve provided on the suction line.

In this way, the working channel, the suction line and the suction control valve provided on the suction line are removable from the endoscope.

The detachably fastenable attachment body can comprise an instrument inlet section which forms an entrance section of the working channel that can be accessed from outside. The instrument inlet section is also removable from the endoscope.

The endoscope can comprise the attachment body detachably fastenable on the control body and an endoscope basic body with the control body onto which the detachably fastenable attachment body can be applied, wherein the endoscope basic body does not comprise the working channel assembly and the suction device assembly.

As the endoscope basic body does not comprise the working channel assembly and the suction device assembly, when reusing the cleaned endoscope basic body, which is now fitted with a new, unused attachment body with a new working channel assembly and a new suction device assembly, the risk of contamination through impurities or biofilms resulting from a previous use of the endoscope is massively reduced.

The detachably fastenable attachment body can be designed as a single-use body that can be disposed of after use. The detachably fastenable endoscope basic body can be designed as a multiple-use body that can be cleaned after use and reused.

The clear separation ensures safe use of the endoscope. As a multiple-use body, the endoscope basic body contains the electronic components of the endoscope. Moreover, the attachment body, configured as a single-use body, can be cost-effectively produced as it only has a detachable housing section, the working channel assembly and the suction device assembly and does not comprise the more costly electronic components.

The control body can comprise an incomplete housing, that can be completed with a completion component that is integrated into the detachably fastenable attachment body. The structure and separation of the incomplete housing and the completion component are simple and uncomplicated. The assembly and separation of the incomplete housing and the completion components can be carried out quickly and reliably.

The control body can comprise a housing basic element as an incomplete housing, that through completion with a housing addition section as a completion component forms the control body, wherein the housing addition section is arranged on the detachably fastenable attachment body and comprises the suction control valve. It is the housing, as the component group with which the user works, which provides definite information about whether the attachment body is already mounted on the endoscope or not. The user immediately recognises whether the control body is complete or not. Inadvertent use of an endoscope not yet fitted with the attachment body is immediately recognised and can be prevented.

The suction line can comprise a proximal suction line section, that can be connected to a suction source, and a distal suction line section that extends to the distal end of the endoscope. The suction control valve can be arranged between the proximal suction line section and the distal suction line section. Therefore, the proximal suction line section, that is connectable to the suction source, is also removable from the endoscope together with the suction control valve and the distal suction line section.

The incomplete housing of the control body can have a groove running perpendicularly to the direction of extension of the control body, into which a section of the completion component of the attachment body can be fitted. The completion component can be applied to the incomplete housing in an easy, simple and unequivocally identifiable, as well as quick and uncomplicated manner, in order to complete the endoscope.

The incomplete housing of the control body and/or the attachment body can comprise snap-in fastening means for applying the attachment body to the incomplete housing of the control body. In this way, the completion component can be securely arranged on the incomplete housing of the control body. Inadvertent, unintentional detachment of the completion component from the incomplete housing of the control body is prevented by the snap-in fastening means.

The working channel assembly and the suction device assembly of the fastenable attachment body can be detachably fastened in the control body. When the working channel assembly and the suction device assembly are detachably fastened in the control body, they cannot be accessed from outside. The wall of the control body conceals the working channel assembly and the suction device assembly. The wall concealing the working channel assembly and the suction device assembly can form part of the fastenable attachment body. Alternatively, the wall concealing the working channel assembly and the suction device assembly can be separate from the fastenable attachment body.

The aforementioned aspects of the present invention can be suitably combined.

EMBODIMENTS

Figure 1:
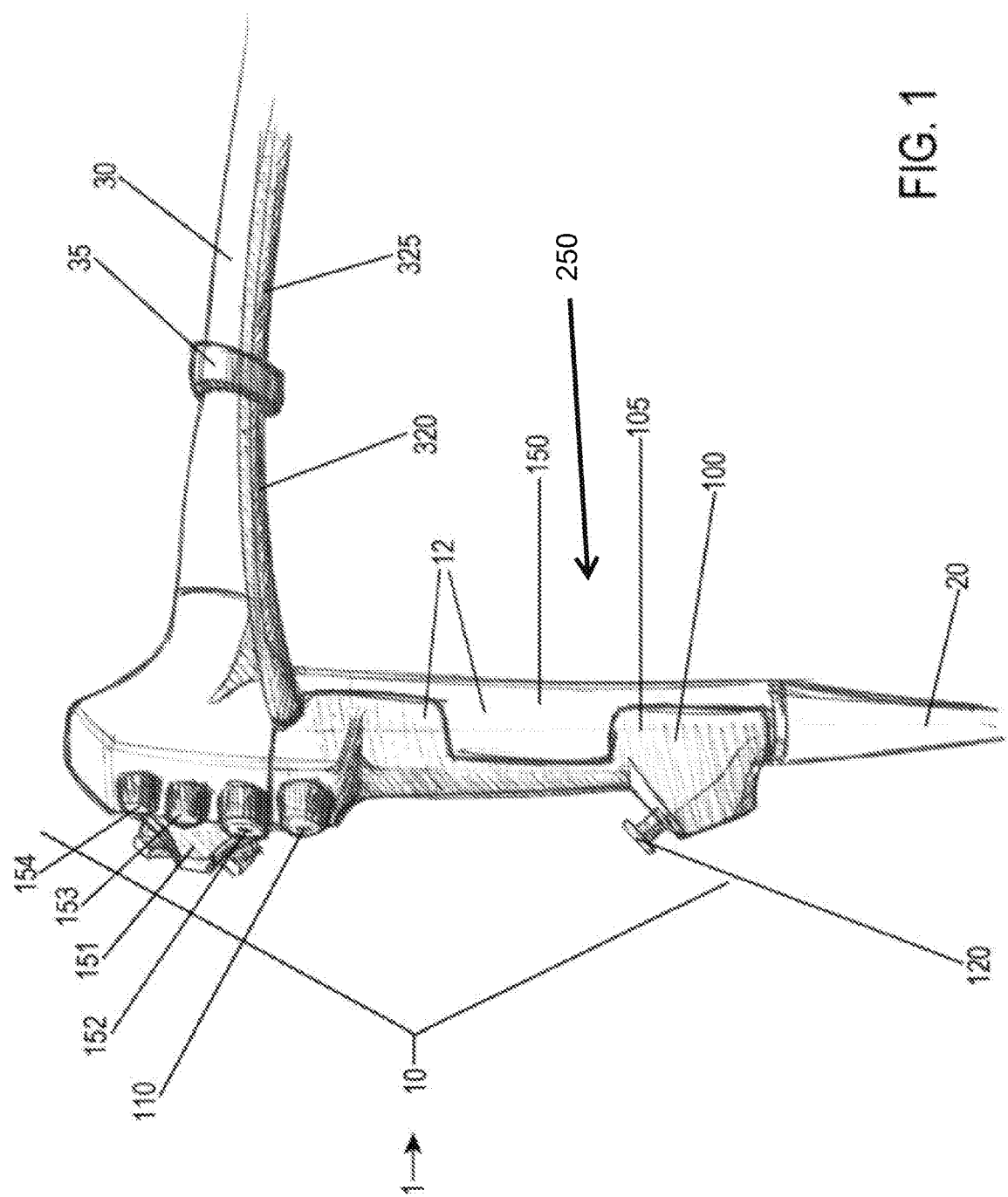
FIG. 1 shows a schematic perspective view of the endoscope according to the invention with a control body in a first embodiment.
Figure 2:
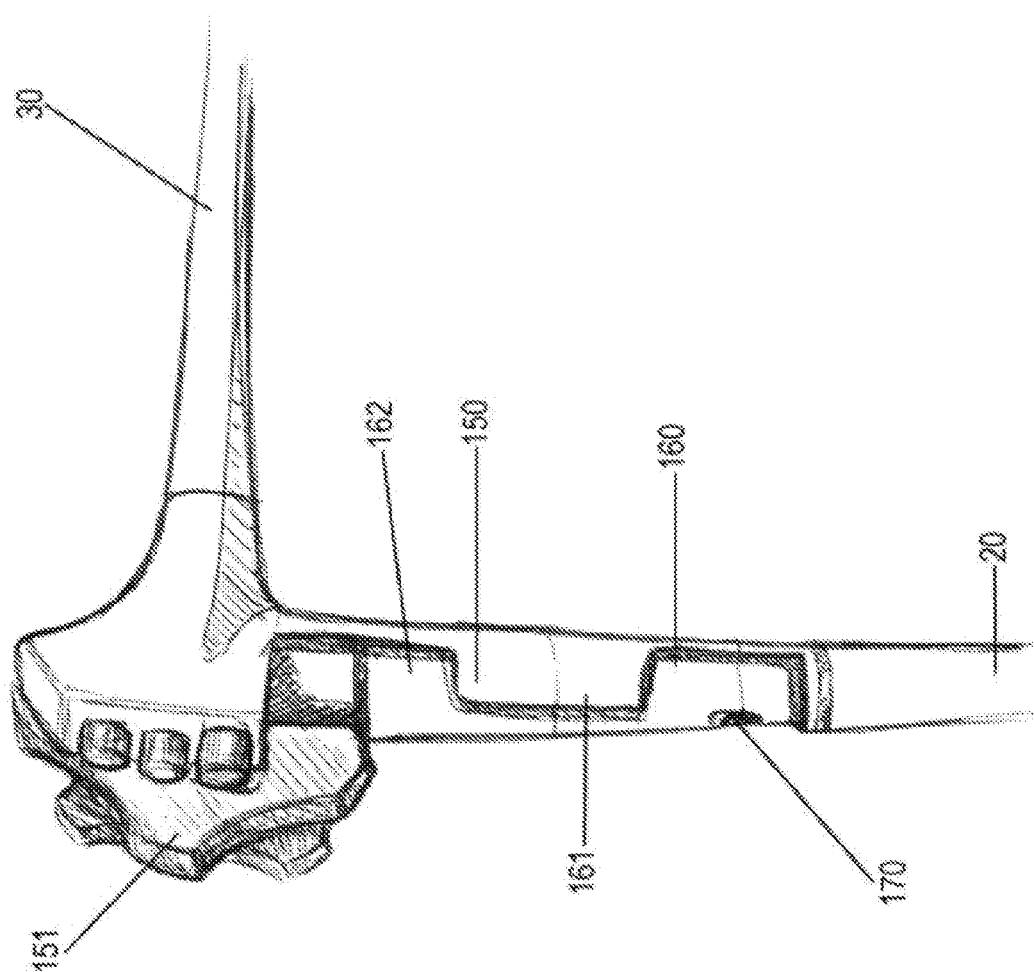
FIG. 2 shows a schematic perspective view of the endoscope of the first embodiment according to the invention, wherein an attachment body is not mounted on an incomplete housing of the control body.
Figure 3:
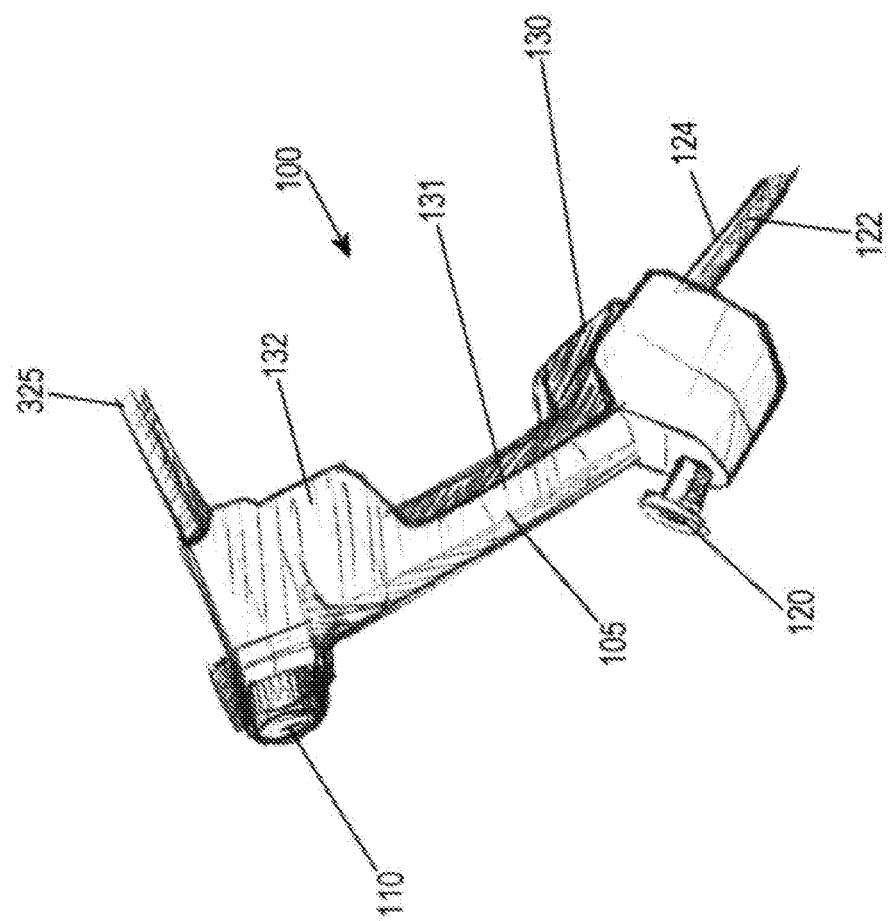
FIG. 3 shows a schematic perspective view of a central section of the attachment body of the first embodiment.

The present invention is described in more detail below by way of exemplary embodiments with reference to drawings. The illustrations in the drawings are not necessarily true to scale, but may be distorted for the sake of improved clarity.

First Embodiment

Below, a first embodiment of the present invention is described with reference to FIGS. 1 to 4.

An endoscope 1 according to the invention has a control body 10, an insertion tube 20 and a supply cable 30.

The insertion tube 20 is connected to the control body 10 at the distal side of the control body 10. Arranged on the distal side of the insertion tube 20 is a distal end section 40. With the distal end section 40 first, the insertion tube 20 is inserted into a patient for the purpose of an examination or surgical intervention. In the insertion tube 20, a working channel described below extends up to the distal end section 40.

The supply cable 30 is connected to the control body 10 on the proximal side of the control body 10. The supply cable 30 comprises an electrical line for supplying the control body 10 with electricity. The supply cable 30 also comprises a signal cable that transmits data obtained by the endoscope to a (not shown) evaluation unit. The supply cable 30 has a plug which is inserted into the evaluation unit on the proximal side of the supply cable 30.

As a housing basic element, the control body 10 has an incomplete housing 150 that only forms a complete housing after the application of a completion component 105. The completion component 105 acts as a housing addition section to complete the housing of the control body 10. The complete housing of the control body 10 is ergonomically formed and designed so that in the middle area—seen in the direction of extension—it has a grip area 12 that can be grasped by the hand. The user grasps the grip area 12 in order to use the endoscope. The grip area 12 extends over the incomplete housing 150 and the completion component 105, as is shown in FIG. 1.

The control body 10 has a front side, on which are arranged a suction control valve 110, a water-air valve 152, control buttons 153 and 154 and an instrument inlet section 120, which forms an entrance section of the working channel that is accessible from outside, see FIG. 1.

More specifically, the suction control valve 110 and the instrument inlet section 120 are arranged on the completion component 105. The water-air valve 152 and the control buttons 153 and 154 are arranged on the incomplete housing 150. The water-air valve 152 serves to switch on/switch off the air and/or water supply from a not shown supply source and controls, for example, the rinsing with water at the distal end. The air and/or water supply and the water-air valve 152 can be used as in conventional endoscopes. The control buttons 153 and 154 are freely assignable and can, for example, be control buttons with processor functions, such as a button for taking a screenshot of a scenario observed by a camera at the distal end, a button for zooming an image displayed on a monitor of the scenario observed by the camera, or similar.

Arranged on a lateral side of the incomplete housing 150 is a control wheel 151 that serves for controlling a deflection movement of the distal section, for example. The control wheel 151 can also have other functions.

The incomplete housing 150 is designed in such a way that it is open on the front side. On the front side of the incomplete housing 150, the incomplete housing 150 is closed by way of the completion component 105. Therefore, on its front side the incomplete housing 150 has a circumferential section, the shape of which is complementary to the circumferential section of the completion component 105. In other words, the shape of the circumferential section of the completion component 105 is matched to the shape of the circumferential section of the incomplete housing 150. For this reason, in the embodiment, the circumferential section of the incomplete housing 150 has a first (distal) groove 160 and a second (proximal) groove 162. Between the first groove 160 and the second groove 162 a raised section 161 projects to the front side.

At the edges of each of the first groove 160 and of the second groove 163, a perpendicular edge of the raised section 161 projects to the front side. The perpendicular edges of the raised section 161 extend perpendicularly to the direction of extension of the incomplete housing 150 and thus perpendicularly to the direction of extension of the control body 10.

In the area that is exposed through the absence of the completion component 105, the incomplete housing 150 also has an opening 170 for a working channel element 122, as is described below. The opening 170 forms an entrance to a channel that extends to the distal end section 40 and through which the working channel element 122 can be pushed.

The incomplete housing 150 comprises snap-in fastening means 400 on the edge of the opening that is formed by the first groove 160, the raised section 161 and the second groove 162.

The completion component 105 is part of an attachment body 100, which is applied to the incomplete housing 150. Without this attachment body 100, the endoscope is still a not yet complete endoscope basic body which must be completed with the attachment body 100 in order to be used.

The attachment body 100 comprises the completion component 105, a working channel assembly and a suction device assembly. The working channel assembly and the suction device assembly of the fastenable attachment body 100 are detachably fastened in the control body 10.

The completion component 105 forms the additional housing section for completing the incomplete housing 150. The shape of the circumferential section of the completion component 105 is matched to the shape of the circumferential section of the incomplete housing 150. Thus, in the embodiment, the circumferential section of the completion component 105 has a first (distal) projection 130 and a second (distal) projection 132. Between the first projection 130 and the second projection 132, a recess 131 is formed. The raised section 161 of the incomplete housing 150 fits into the recess 131.

Extending respectively at the edges of the first projection 130 and of the second projection 132 is a perpendicular edge of the recess 131. The perpendicular edges of the recess 131 extend perpendicularly to the direction of extension of the completion component 105.

The completion component 105 has counterparts to the snap-in fastening means 400 on the opening edge which is formed by the first projection 130, the recess 131 and the second projection 132. Because of the snap-in fastening means 400 on the incomplete housing 150, the completion component 105 can engage on the incomplete housing 150.

The type of snap-in fastening means 400 can be freely selected. As snap-in fastening means 400, a snap-in connection can, for example, be selected in the form of barbed hooks which engage in corresponding openings as counterparts on the completion component 105. Any snap-in fastening means 400 can be used.

Arranged on the front side of the completion component 105 is the instrument inlet section 120. The instrument inlet section 120 is part of the working channel assembly.

The working channel assembly comprises a working channel element 122. When the working channel element 122 is completely introduced into the insertion tube 20, the working channel element 122 extends up to the distal end of the endoscope 1.

The working channel element 122 is tubular and forms a channel surrounded by a casing that serves as a working channel, through which instruments can be guided to the distal end of the working channel element 122. The proximal end of the working channel element 122 is formed by the instrument inlet section 120. On its inner circumference the instrument inlet section 120 has a rubber seal.

The outer diameter of the working channel element 122 is chosen in such a way that the working channel element 122 fits into the opening 170 so that the working channel element 122 can be reliably pushed to the distal end of the endoscope 1.

Arranged on the front side of the completion component 105 is the suction control valve 110. The suction control valve no is part of the suction device assembly.

Figure 5:
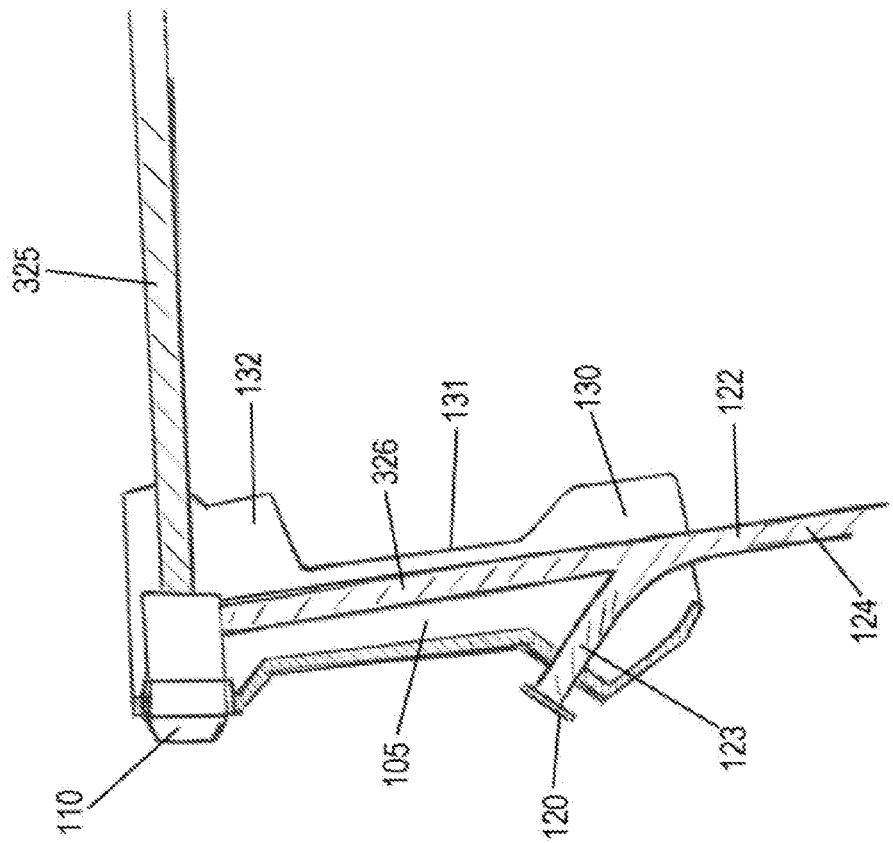
FIG. 5 shows a schematic cross-sectional view of the control body of the first embodiment.

The suction device assembly comprises a suction line 320. The suction line 320 is formed by a channel-like line which comprises a proximal suction line section 325, connectable to a (not shown) proximal suction source (negative pressure source), and a distal suction line section 326. The distal suction line section 326 extends to the working channel element 122 and opens out into this, see FIG. 5. The suction control valve 110 is arranged between the proximal suction line section 325 and the distal suction line section 326. Through operating the suction control valve 110, the suction line 320 is opened or closed. Through operation to open the suction control valve 110, the negative pressure of the suction source acts at the distal end of the suction line 320. Through operation to close the suction control valve 110, the suction line 320 is closed so that the negative pressure of the suction source no longer acts at the distal end of the suction line 320.

The proximal suction line section 325 projects at the proximal side of the completion component 105. On its proximal side, the proximal suction line section 325 has a (not shown) connection element that is connectable to the suction source.

When the attachment body 100 is arranged on the incomplete housing 150, the proximal suction line section 325 is guided on the outer edge of the incomplete housing 150 and on the supply cable 30. More particularly, on the supply cable 30, a ring element 35 is provided as a fastening means. The proximal suction line section 325 is pushed through the ring element 35. Along the supply cable 30, several ring elements 35 can be provided. In this way, the proximal suction line section 325 can extend in parallel to and closely adjoining the supply cable 30, see FIG. 1.

The distal suction line section 326 is integrated into the working channel element 122. More particularly, the distal suction line section 326 and the working channel element 122 form a Y shape. The working channel element 122 is divided into a proximal working channel section 123 and a distal working channel section 124. The proximal working channel section 123 extends from the instrument inlet section 120 to the junction point between the distal suction line section 326 and the working channel element 122. The distal working channel section 124 extends from the junction point between the distal suction line section 326 and the working channel element 122 to the distal end of the endoscope.

When the attachment body 100 is arranged on the incomplete housing 150, the distal working channel element section 124 is fully inserted through the opening 170 into the insertion tube 20, wherein the distal suction line section 326 extends to the distal end of the endoscope 1. The working channel element 122 is thus pushed into the opening 170.

As described above, the suction line 320 opens out into the working channel element 122. Looked at in another way, the endoscope 1 has a continuous channel element from the suction source to the distal end of the working channel. On the completion component 105 a lateral access to this channel element is provided. The access has, as the entrance, the instrument inlet section 120 and opens into the channel element.

At the distal end section 40 of the endoscope 1, the distal working channel element section 124 jointly forming the working channel and the suction channel, is open.

Figure 6:
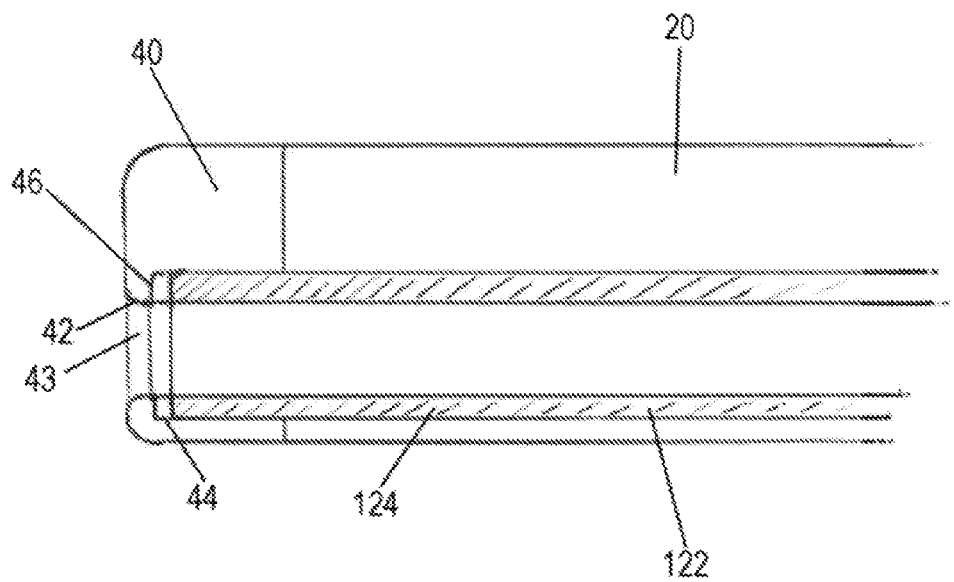
FIG. 6 shows a schematic cross-sectional view of the control body of the endoscope of the first embodiment.

The details of the distal end section 40 of the endoscope 1 are shown in FIG. 6. It should be noted here that FIG. 6 only shows the transition from the insertion tube 20 to the distal end section 40 schematically as an illustration of the principle. The invention is not restricted to this depiction. The distal end section 40 can have various elements which are not shown, e.g. lighting, a camera, a rinsing nozzle etc.

The distal end section 40 has an opening 42 on the distal side. The distal working channel section 44 of the working channel is provided in the distal end section 40. At the opening 42, the distal working channel section 44 has a section 43 with a reduced diameter. On the proximal side of the section 43 with a reduced diameter, the distal working channel section 44 forms a shoulder surface 46 extending outwards from the section 43 with a reduced diameter. The inner diameter of the section 43 with a reduced diameter corresponds to the inner diameter of the distal working channel section 124.

The distal working channel section 44 therefore has an inner diameter that is greater than the inner diameter of the opening 42.

The distal working channel element section 124 can therefore be pushed into the distal working channel section 44 up to the shoulder surface 46.

The distal working channel element section 124 cannot be pushed over the shoulder surface 46. In the furthest pushed position in the distal direction, the distal working channel element section 124 is in contact with the shoulder surface 46.

In this way, the endoscope 1 according to the invention is divided into an endoscope basic body 250 and the attachment body 100. All mechanical and electronic parts are arranged in the endoscope basic body 250. Not arranged in the endoscope basic body 250 are the elements of the working channel assembly and suction device assembly of the endoscope 1 that have to be cleaned after use of the endoscope 1.

Arranged in the attachment body 100 are the elements of the working channel assembly and the suction device assembly of the endoscope 1. The working channel assembly and the suction device assembly in particular are exposed to contamination when the endoscope 1 is used. Therefore, the elements of the endoscope 1 that can be particularly heavily contaminated during use are accommodated in the attachment body 100.

Function

Figure 4:
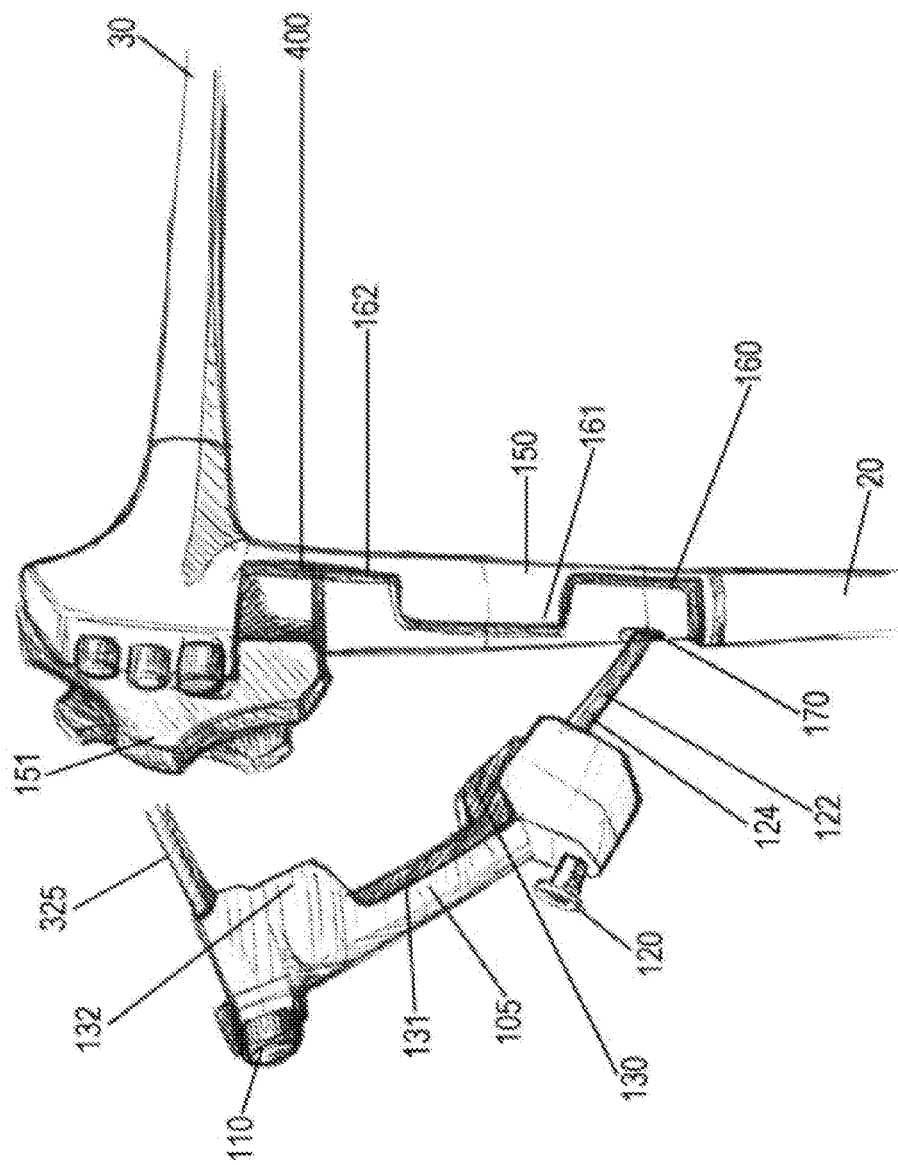
FIG. 4 shows a schematic perspective view of the endoscope of the first embodiment according to the invention, wherein the attachment body is mounted on the incomplete housing of the control body.

For initial use of the endoscope 1, a new attachment body 100 is inserted on the endoscope basic body as shown in FIG. 4. For this, the proximal suction line section 325 is pushed through the ring element 35 on the supply cable 30 (see FIG. 1) and connected to the suction source.

The working channel element 122 is pushed into the opening 170.

Finally, the completion component 105 is placed on the incomplete housing 150, in that the circumferential section with the first projection 130, the recess 131 and the second projection 132 is mounted on the circumferential section of the incomplete housing 150 with the first groove 160, the raised section 161 and the second groove 162 perpendicularly to the direction of extension of the incomplete housing 150. The first projection 130 fits into the first groove 160. The recess 131 fits the raised section 161. The second projection 132 fits into the second groove 162. Through the snap-in fastening means 400, the completion component 105 is firmly engaged on the incomplete housing 150.

The endoscope 1 is now ready for use. The endoscope 1 can be inserted into the patient. Instruments can be introduced through the instrument inlet section 120. Suction can take place via the combined working channel/suction channel.

After use of the endoscope 1, the attachment body 100 is removed from the endoscope basic body. The attachment body 100 can be disposed of.

The remaining endoscope basic body that has been released from the used attachment body 100, can now be cleaned and sterilised and then dried and stored.

To use the endoscope 1 again, the cleaned and reprocessed endoscope basic body is provided with a new attachment body 100.

Advantages

The endoscope 1 can be divided into the endoscope basic body and the attachment body 100. The endoscope basic body with the incomplete housing 150, the insertion tube 20 and the supply cable 30 is reusable and can be cleaned and reprocessed after use.

Arranged in the attachment body 100 are the elements of the working channel assembly and the suction device assembly of the endoscope 1. After use, the attachment body 100 can be disposed of.

To use the endoscope 1 again, the cleaned and reprocessed endoscope basic body is provided with a new attachment body 100 which can be removed from a sterile package shortly before attachment to the endoscope basic body.

In this way, contamination on the endoscope 1 through impurities originating from a previous use can be better prevented when the endoscope 1 is used again.

Particularly the working channel and the suction channel are channels in which a biofilm can form on the inner walls of the channel during use. During reprocessing after the use of an endoscope, such a biofilm can be particularly difficult to remove. As in the present invention, specifically those sections of an endoscope on which the formation of a biofilm is likely, namely the working channel and the suction channel, are moved into the attachment body 100 that can be disposed of after use, the probability of biofilm formation on the surfaces of the reusable endoscope basic body can be massively reduced. Through this, the danger of cross-contamination, whereby germs from one patient are transmitted to another, can be drastically reduced.

The cleaning of the used endoscope basic body is less costly and complicated in comparison with a conventional endoscope, as the working channel assembly and the suction device assembly, as the principally contaminated elements, have been removed.

As the grip area 12 extends over the incomplete housing 150 and the completion component 105, it can be reliably concluded from the shape of the incomplete housing 150 that the completion component 105 is missing and that the endoscope 1 is not yet complete. Incorrect use of the endoscope 1 can be prevented.

The perpendicular edges of the raised section 161 that project to the front side extend perpendicularly to the direction of extension of the incomplete housing 150. As a result, the completion component 105 can be securely pushed onto the housing 150.

In the present invention, in order to assemble the attachment body 100 on the endoscope basic body, the working channel assembly and the suction device assembly are positioned accordingly (proximal suction line section 325 to the proximal side into the ring element 35; working channel element 122 into the opening 170), and the completion component 105 is pushed onto the incomplete housing 150 and clicked on. In this way the endoscope 1 can assembled in a quick and uncomplicated manner.

The attachment body 100 can also be simply, easily and rapidly removed from the endoscope basic body.

As the working channel and the suction line are combined as one channel distally of the junction point, this one channel can have a small diameter, which is suitable for the respective purpose of pushing through the desired instrument and also suction. The receiving channel 44 that is formed in the insertion tube 20 and in the distal end section 40 and at the entrance comprises the opening 170 can thus also have a small diameter. The outer diameter dimension of the insertion tube 20 and of the distal end section can thus be correspondingly small.

Since the distal working channel element section 124 cannot be pushed beyond the shoulder surface 46 and since in the furthest pushed position of the working channel element section 124 in the distal direction it rests on the shoulder surface 46, the working channel element 122 does not come into contact with the patient when being used. Only the distal end section 40 surrounding the working channel element 122 comes into contact with the patient. In this way, the working channel element 122 is more protected from impurities.

Second Embodiment

Figure 7:
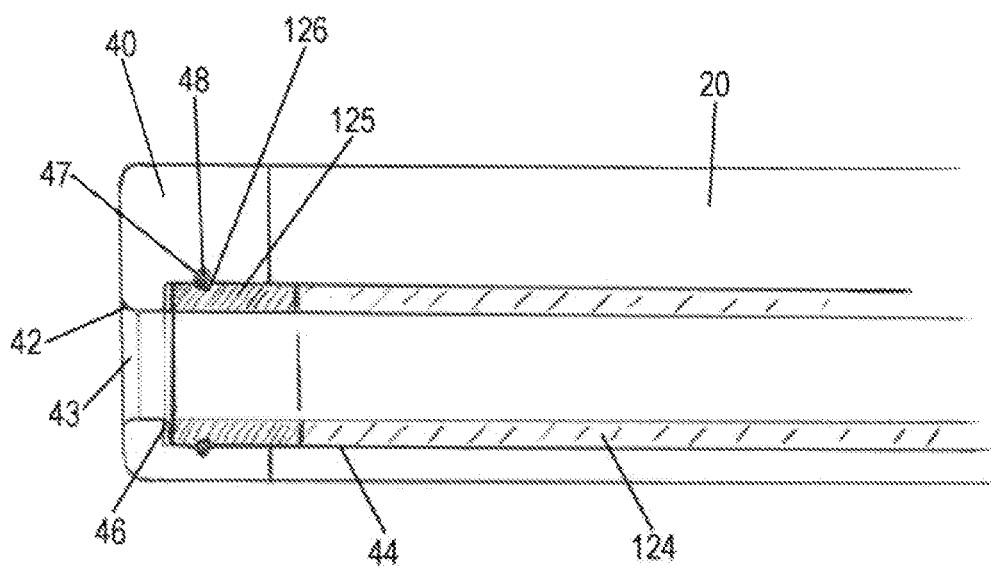
FIG. 7 shows a schematic cross-sectional view of the distal end of an endoscope of a second embodiment.

With reference to FIG. 7 a second embodiment is described. In the second embodiment, the distal area of the distal working channel element section 124 has been modified. The remaining structure is the same as in the first embodiment.

The distal working channel element section 124 has a distal end region 125. On the outer surface of the distal end region 125, the distal end region 125 is provided with a circumferential recess 126. The circumferential recess 126 extends along the outer circumference of the distal end region 125.

On the inner surface of the distal working channel 44, the distal working channel section 44 is provided with a circumferential recess 47. The circumferential recess 47 extends along the inner circumference of the distal working channel section 44.

The circumferential recess 47 is more deeply recessed into the distal working channel section 44 than the circumferential recess 126 in the distal end region 125. A holding element 48 is firmly inserted in the circumferential recess 47.

The holding element 48 can be designed as a ring element. The holding element 48 can be a sealing ring. The holding element 48 can also be a spring element or another elastic element.

In the situation in which the working channel element 122 is pushed into the endoscope 1, i.e. completely (fully) pushed into the insertion tube 20 and distal end section 40, the circumferential recess 126 of the distal working channel element section 145 and the circumferential recess 47 of the distal working channel section 44 are opposite each other. In this assembled state, the holding element 48 of the distal end section 40 engages in the circumferential recess 126 of the distal working channel element section 124. Through this, in the assembled state the distal working channel section 44 can snap into the distal end section 40. In this way the distal working channel section 44 can be securely held on the distal end section 40. In this embodiment too, the working channel element 122 does not come into contact with the patient.

Third Embodiment

Figure 8:
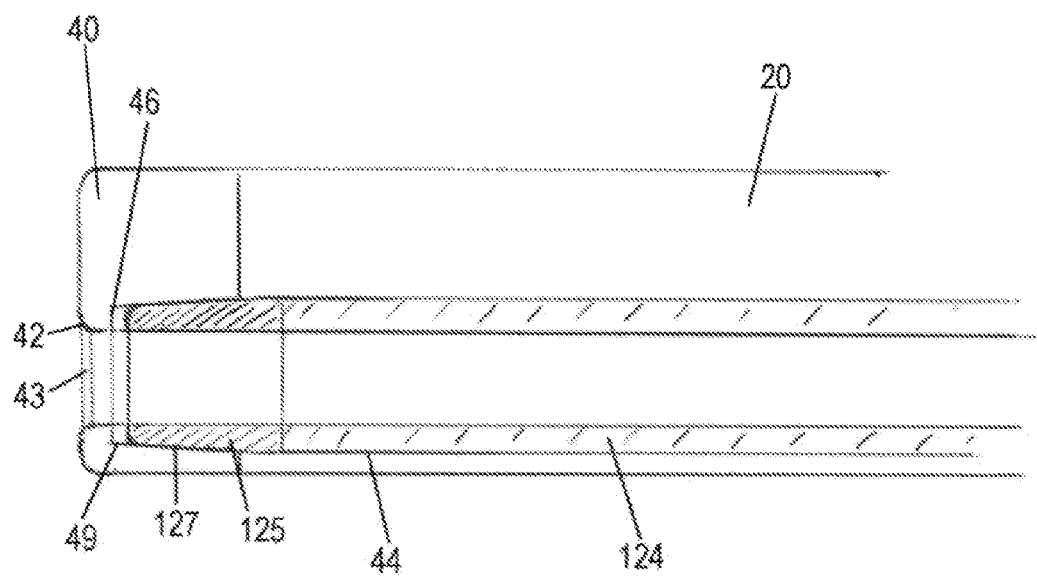
FIG. 8 shows a schematic cross-sectional view of the distal end of an endoscope of a third embodiment.

With reference to FIG. 8 a third embodiment is described. In the third embodiment, the distal region of the distal working channel element section 124 has been modified. The remaining structure is the same as in the first embodiment.

The distal working channel element section 124 has a distal end region 125. On the outer surface of the distal end region 125, the distal end region 125 is provided with a conical outer surface 127. The conical outer surface 127 narrows in the distal direction of the distal end region 125. The outer diameter of the distal end region 125 therefore decreases in the distal direction of the distal end region 125.

At the distal end, on the inner surface of the distal working channel section 44, the distal working channel section 44 is provided with a conical inner surface 49. The conical inner surface 49 narrows in the distal direction of the distal working channel section 44. In other words, on the conical inner surface 49, the inner diameter of the distal working channel section 44 decreases in the distal direction of the distal working channel section 44.

The slant of the conical inner surface 49 corresponds to the slant of the conical outer surface 127.

In the situation in which the working channel element 122 is completely (fully) pushed into the endoscope 1 and into the distal end section 40, the conical outer surface 127 of the distal working channel element section 124 rests on the conical inner surface 49 of the distal end section 40 and cannot be moved any further in the distal direction.

Through this, in the assembled state the distal working channel section 44 can adjoin the distal end section 40 in a contact position. In this way the distal working channel section 44 can be securely held on the distal end section 40. In this embodiment too, the working channel element 122 does not come into contact with the patient.

Other Alternatives

In the first embodiment a control wheel 151 is described. The endoscope can comprise several control wheels for various purposes.

The control wheel 151 can be omitted if the invention is used, for example, in an endoscope whose distal section cannot be deflected.

In the first embodiment, the circumferential section of the incomplete housing 150 comprises the first (distal) groove 160 and the second (proximal) groove 162 and the raised section 161 between the grooves 160, 162, which match the projections 130 132 and the recess 131 of the completion component 105 which are designed as counterparts. The invention is not restricted to this. The precise shape of the circumferential section of the incomplete housing 150 and its apposite counter-shape on the completion component 105 can be freely selected. The user should only be able to recognise that the casing without the completion component 105 is incomplete. Furthermore, it must only be guaranteed that the completion component 105 fits onto the incomplete housing 150.

In the situation in which the completion component 105 is applied on the incomplete housing 150, in the first embodiment the proximal suction line section 325 on the outer side of the incomplete housing 150 extends in the proximal direction. In an alternative, in the incomplete housing 150 on the proximal side a channel with a (distal) opening is provided, which similar to the opening 170 is here designed for the proximal suction line section 325. On the proximal side, this channel opens out on the outer side of the incomplete housing 150 close to the connection point of the supply cable 30 on the incomplete housing 150. Through this channel, the proximal suction line section 325 can be pushed in the proximal direction, whereby it can also run along the supply cable 30 in a parallel and closely adjoining manner. This improves the optical appearance, as on the grip area 12 of the control body 10 itself, no section of the suction line 320 is exposed.

In the first embodiment, on the supply cable 30, the ring element 35 is provided as a fastening means for the proximal suction line section 325. Any other fastening means can be used as alternatives. For example, a clamp, a strap or Velcro strip can be used for this.

In the first embodiment the working channel element 122 is pushed into the opening 170. The working channel element 122 is connected to the distal suction line section so that the working channel in the working channel element 122 can also be used as a suction line. In an alternative, two tube elements (channel elements) are arranged on the completion component 105 pointing in the distal direction. Namely, a distal suction line section and a working channel element can be formed as two separate tube elements which extend to the distal end of the endoscope 1. One of these tube elements is the working channel element of the working channel assembly. The other tube element is the distal suction line section. The distal suction line section and the working channel element are pushed into the opening 170. The opening 170 and its channel up to the distal end are of a size which allows the incorporation of the distal suction line section and the working channel element. When the suction line section and working channel element are completely introduced into the insertion tube 20, the suction line section and the working channel element extend up to the distal end of the endoscope 1.

In a further alternative, the distal suction line section and the working channel element are designed as a one-piece structure. In the one-piece design, the distal suction line section and the working channel element form a joint tube element, the inner space of which is divided by a partition element into two chambers, which each extend to the distal end of the endoscope 1. The one-piece design results in a particularly small construction, since the channel with the opening 170 in the insertion tube 20 can be reduced in size accordingly. The joint tube element can be produced by extrusion. On the proximal section of the joint tube element, the joint tube element can be connected in such a way that the proximal section of the distal is connected on the suction control valve 100 and the proximal section of the working channel element is connected on the instrument inlet section 120.

In a further alternative, the detachably fastenable attachment body 100, which comprises the working channel assembly and the suction device assembly, is formed without the completion component 105. This detachably fastenable attachment body can be removed through an opening on the endoscope, for example on the control body 10. The control body 10 then has a complete housing. In this alternative too, the working channel assembly and the suction device assembly of the fastenable attachment body 100 are detachably fastened in the control body 10.

The invention can be advantageously used in a flexible endoscope. More particularly, the invention can be advantageously used in a gastrointestinal endoscope. The principle of the invention can also be used in any other type of endoscope.

LIST OF REFERENCE NUMBERS

1 Endoscope
10 Control body
12 Grip area
20 Insertion tube
30 Supply cable
35 Fastening means
40 Distal end section
42 Opening
43 Section with reduced diameter
44 Distal working channel section
46 Shoulder surface
47 Circumferential recess
48 Holding element
49 Conical inner surface
100 Attachment body
105 Additional housing section, completion component
110 Suction control valve
120 Instrument inlet section
122 Working channel element
123 Proximal working channel element section
124 Proximal working channel element section
125 Distal end area
126 Circumferential recess
127 Conical outer surface
130 Projection
131 Recess
132 Projection
150 Incomplete housing
151 Control wheel
152 Water-air valve
153 Control button
154 Control button
160 Groove
161 Raised section
162 Groove
170 Opening for working channel element
320 Suction line
325 Proximal suction line section
326 Distal suction line section
400 Snap-in fastening means

The invention claimed is:
1. An Endoscope comprising:
a working channel in an insertion tube;
a control body, on the distal side of which the insertion tube is connected, the control body comprising an incomplete housing comprising a snap-in fastener; and
an attachment body detachably fastenable to the control body and comprising:
a working channel assembly;
a suction device assembly; and
a housing completion component detachably fastenable to the incomplete housing via the snap-in fastener, wherein the housing completion component fastened to the incomplete housing together form a grip between the working channel assembly and the suction device assembly, which is configured to be grasped by a user, wherein:
the working channel assembly comprises the working channel, which extends to the distal end of the endoscope, and
the suction device assembly comprises a suction line and a suction control valve provided on the suction line.
2. The Endoscope according to claim 1, wherein
the detachably fastenable attachment body comprises an instrument inlet section which forms an entrance section of the working channel that can be accessed from outside.
3. The Endoscope according to claim 1, wherein
the endoscope comprises the attachment body and an endoscope basic body comprising the control body, and
wherein the endoscope basic body does not comprise the working channel assembly and the suction device assembly.
4. The Endoscope according to claim 3, wherein
the detachably fastenable attachment body is designed as a single-use body that can be disposed of after use, and
the endoscope basic body is designed as a multiple-use body that can be cleaned after use and reused.

5. The Endoscope according to claim 1, wherein
the suction line comprises a proximal suction line section, that can be connected to a suction source, and a distal suction line section that extends to the distal end of the endoscope, and
the suction control valve is arranged between the proximal suction line section and the distal suction line section.

6. The Endoscope according to claim 1, wherein
the incomplete housing of the control body has a groove running perpendicularly to the direction of extension of the control body, into which a section of the housing completion component of the attachment body can be fitted.

7. The Endoscope according to claim 1, wherein
the working channel assembly and the suction device assembly of the attachment body are detachably fastened in the control body.

* * * * *